United States Patent
Linhardt et al.

(10) Patent No.: US 9,289,954 B2
(45) Date of Patent: Mar. 22, 2016

(54) METHOD OF RING-SHAPED STRUCTURE PLACEMENT IN AN EYE-MOUNTABLE DEVICE

(71) Applicant: Verily Life Sciences LLC, Mountain View, CA (US)

(72) Inventors: Jeffrey George Linhardt, Pleasanton, CA (US); Harvey Ho, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 359 days.

(21) Appl. No.: 13/743,443

(22) Filed: Jan. 17, 2013

(65) Prior Publication Data

US 2014/0197558 A1   Jul. 17, 2014

(51) Int. Cl.
| | | |
|---|---|---|
| *B29D 11/00* | (2006.01) | |
| *A61B 5/00* | (2006.01) | |
| *G02C 7/04* | (2006.01) | |
| *A61B 5/145* | (2006.01) | |

(52) U.S. Cl.
CPC ...... *B29D 11/00038* (2013.01); *A61B 5/14507* (2013.01); *A61B 5/14532* (2013.01); *A61B 5/6821* (2013.01); *B29D 11/00807* (2013.01); *G02C 7/04* (2013.01)

(58) Field of Classification Search
None
See application file for complete search history.

(56) References Cited

U.S. PATENT DOCUMENTS

| | | |
|---|---|---|
| 3,958,560 A | 5/1976 | March |
| 4,014,321 A | 3/1977 | March |
| 4,055,378 A | 10/1977 | Feneberg et al. |
| 4,122,942 A | 10/1978 | Wolfson |
| 4,136,250 A | 1/1979 | Mueller et al. |

(Continued)

FOREIGN PATENT DOCUMENTS

| | | |
|---|---|---|
| EP | 0369942 | 5/1990 |
| EP | 0686372 | 12/1995 |

(Continued)

OTHER PUBLICATIONS

Bionic contact lens 'to project emails before eyes,' http://www.kurzweilai.netforums/topic/bionic-contact-lens-to-project-emails-before-eyes, Last accessed Mar. 14, 2012, 2 pages.

(Continued)

*Primary Examiner* — Benjamin Schiffman
(74) *Attorney, Agent, or Firm* — McDonnell Boehnen Hulbert & Berghoff LLP

(57) ABSTRACT

Example eye-mountable devices and methods for fabricating eye-mountable devices are described. A method may include applying a first amount of polymerizable material to a ring-shaped structure, where the ring-shaped structure comprises at least one sensor configured to detect an analyte. The method also may include positioning the ring-shaped structure with the first amount of polymerizable material applied thereto in a mold, where the mold is configured to form an eye-mountable device. Further, the method may include applying pressure on the ring-shaped structure in the mold while curing the first amount of polymerizable material. Still further, the method may include adding a second amount of polymerizable material to the mold with the ring-shaped structure therein, and curing the second amount of polymerizable material to form an over-molded polymer layer such that the ring-shaped structure is at least partially enclosed in the eye-mountable device.

19 Claims, 10 Drawing Sheets

(56) References Cited

U.S. PATENT DOCUMENTS

| | | |
|---|---|---|
| 4,143,949 A | 3/1979 | Chen |
| 4,153,641 A | 5/1979 | Deichert et al. |
| 4,214,014 A | 7/1980 | Hofer et al. |
| 4,309,085 A | 1/1982 | Morrison |
| 4,312,575 A | 1/1982 | Peyman et al. |
| 4,382,902 A | 5/1983 | Feurer |
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint |
| 5,177,165 A | 1/1993 | Valint et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicolson et al. |
| 5,908,906 A | 6/1999 | Kunzler et al. |
| 5,981,669 A | 11/1999 | Valint et al. |
| 6,087,941 A | 7/2000 | Ferraz et al. |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,579,918 B1 * | 6/2003 | Auten et al. ........... 523/106 |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Müller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 2002/0193674 A1 | 12/2002 | Fleischman et al. |
| 2003/0035083 A1 | 2/2003 | Francis et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0221276 A1 | 10/2005 | Rozakis et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2009/0206498 A1 * | 8/2009 | Tepedino et al. ............ 264/1.36 |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0103368 A1 | 4/2010 | Amirparviz et al. |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |

(56) References Cited

U.S. PATENT DOCUMENTS

| | | | |
|---|---|---|---|
| 2012/0075168 | A1 | 3/2012 | Osterhout et al. |
| 2012/0075574 | A1 | 3/2012 | Pugh et al. |
| 2012/0078071 | A1 | 3/2012 | Bohm et al. |
| 2012/0088258 | A1 | 4/2012 | Bishop et al. |
| 2012/0092612 | A1 | 4/2012 | Binder et al. |
| 2012/0109296 | A1 | 5/2012 | Fan |
| 2012/0177576 | A1 | 7/2012 | Hu |
| 2012/0199995 | A1 | 8/2012 | Pugh et al. |
| 2012/0201755 | A1 | 8/2012 | Rozakis et al. |
| 2012/0245444 | A1 | 9/2012 | Otis et al. |
| 2012/0259188 | A1 | 10/2012 | Besling |

FOREIGN PATENT DOCUMENTS

| | | |
|---|---|---|
| EP | 1061874 | 12/2000 |
| EP | 1818008 | 8/2007 |
| EP | 1947501 | 7/2008 |
| EP | 1617757 | 8/2009 |
| EP | 2457122 | 5/2012 |
| JP | 06208090 | 7/1994 |
| JP | 08194193 | 7/1996 |
| WO | 95/04609 | 2/1995 |
| WO | 01/16641 | 3/2001 |
| WO | 01/34312 | 5/2001 |
| WO | 03/065876 | 8/2003 |
| WO | 2004/060431 | 7/2004 |
| WO | 2004/064629 | 8/2004 |
| WO | WO 2004/064629 A1 | 8/2004 |
| WO | 2006/015315 | 2/2006 |
| WO | 2009/094643 | 7/2009 |
| WO | 2010/105728 | 9/2010 |
| WO | 2010/133317 | 11/2010 |
| WO | 2011011344 | 1/2011 |
| WO | 2011/034592 | 3/2011 |
| WO | 2011/035228 | 3/2011 |
| WO | 2011/035262 | 3/2011 |
| WO | 2011/083105 | 7/2011 |
| WO | 2011/163080 | 12/2011 |
| WO | 2012/035429 | 3/2012 |
| WO | 2012/037455 | 3/2012 |
| WO | 2012/051167 | 4/2012 |
| WO | 2012/051223 | 4/2012 |
| WO | 2012052765 | 4/2012 |

OTHER PUBLICATIONS

Brahim, et al., "Polypyrrole-hydrogel composites for the construction of clinically important biosensors," 2002, Biosensors & Bioelectronics, pp. 53-59, vol. 17.
Chen, et al., "Microfabricated Implantable Parylene-Based Wireless Passive Intraocular Pressure Sensors," Journal of Microelectromechanical Systems, Dec. 2008, pp. 1342-1351, vol. 17, No. 6.
Chu, et al., "Soft Contact-lens Sensor for Monitoring Tear Sugar as Novel Wearable Device of Body Sensor Network," http://www.ksi edu/seke/dms11/DMS/2_Kohji_Mitsubayashi.pdf, Last accessed Jul. 27, 2012, 4 pages.
"Contact Lenses: Look Into My Eyes," The Economist, Jun. 2, 2011, http://www.economist.com/node/18750624/print, Last accessed Mar. 13, 2012, 8 pages.
Haders, "New Controlled Release Technologies Broaden Opportunities for Ophthalmic Therapies," Drug Delivery Technology, Jul./Aug. 2009, pp. 48-53, vol. 8, No. 7.
Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012. 5 pages.
Huang, et al., "Wrinkling of Ultrathin Polymer Films," Mater. Res. Soc. Symp. Proc., 2006, 6 pages, vol. 924, Materials Research Society.
Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.

Liao, et al., "A 3-µW CMOS Glucose Sensor for Wireless Contact-Lens Tear Glucose Monitoring ," IEEE Journal of Solid-State Circuits, Jan. 2012, pp. 335-344, vol. 47, No. 1.
Liao, et al., "A 3-µW Wirelessly Powered CMOS Glucose Sensor for an Active Contact Lens," 2011 IEEE International Solid-State Circuits Conference, Session 2, Feb. 21, 2011, 3 pages.
Lingley, et al., "A Single-Pixel Wireless Contact Lens Display," Journal of Micromechanics and Microengineering, 2011, pp. 1-8.
Lingley, et al., "Multipurpose integrated active contact lenses," SPIE, 2009, 2 pages.
Liu, et al., "Miniature Amperometric Self-Powered Continuous Glucose Sensor with Linear Response," Analytical Chemistry, 2012, 7 pages.
Loncar, et al., "Design and Fabrication of Silicon Photonic Crystal Optical Waveguides," Journal of Lightwave Technology, Oct. 2000, pp. 1402-1411, vol. 18, No. 10.
Murdan, "Electro-responsive drug delivery from hydrogels," Journal of Controlled Release, 2003, pp. 1-17, vol. 92.
Pandey, et al., "A Fully Integrated RF-Powered Contact Lens With a Single Element Display," IEEE Transactions on Biomedical Circuits and Systems, Dec. 2010, pp. 454-461, vol. 4, No. 6.
Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.
Selner, et al., "Novel Contact Lens Electrode Array for Multi-electrode Electroretinography (meERG)," IEEE, 2011, 2 pages.
Singh , et al., "Novel Approaches in Formulation and Drug Delivery using Contact Lenses," Journal of Basic and Clinical Pharmacy, May 2011, pp. 87-101, vol. 2, Issue 2.
Thomas, et al., "Functional Contact Lenses for Remote Health Monitoring in Developing Countries," IEEE Global Humanitarian Technology Conference, 2011, pp. 212-217, IEEE Computer Society.
Tweedie, et al., "Contact creep compliance of viscoelastic materials via nanoindentation," J. Mater. Res., Jun. 2006, pp. 1576-1589, vol. 21, No. 2, Materials Research Society.
Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.
Zarbin, et al., "Nanotechnology in ophthalmology," Can J Ophthalmol, 2010, pp. 457-476, vol. 45, No. 5.
Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.
Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.
Chu et al., "Biomedical soft contact-lens sensor for in situ ocular biomonitoring of tear contents," Biomed Microdevices, 2011, pp. 603-611, vol. 13.
Chu et al., "Soft contact lens biosensor for in situ monitoring of tear glucose as non-invasive blood sugar assessment," Talanta, 2011, pp. 960-965, vol. 83.
Ho et al., "Contact Lens With Integrated Inorganic Semiconductor Devices," MEMS 2008. IEEE 21st International Conference on. IEEE, 2008., pp. 403-406.
Lähdesmäki et al., "Possibilities for Continuous Glucose Monitoring by a Functional Contact Lens," IEEE Instrumentation & Measurement Magazine, Jun. 2010, pp. 14-17.
Lingley et al., "A contact lens with integrated micro solar cells," Microsyst Technol, 2012, pp. 453-458, vol. 18.
Parviz, Babak A., "For Your Eyes Only," IEEE Spectrum, Sep. 2009, pp. 36-41.
Saeedi, E. et al., "Self-assembled crystalline semiconductor optoelectronics on glass and plastic," J. Micromech. Microeng., 2008, pp. 1-7, vol. 18.
Saeedi et al., "Self-Assembled Inorganic Micro-Display on Plastic," Micro Electro Mechanical Systems, 2007. MEMS. IEEE 20th International Conference on. IEEE, 2007., pp. 755-758.
Sensimed Triggerfish, Sensimed Brochure, 2010, 10 pages.
Shih, Yi-Chun et al., "An Inductorless DC-DC Converter for Energy Harvesting With a 1.2-µW Bandgap-Referenced Output Controller,"

(56) References Cited

OTHER PUBLICATIONS

IEEE Transactions on Circuits and Systems-II: Express Briefs, Dec. 2011, pp. 832-836, vol. 58, No. 12.

Shum et al., "Functional modular contact lens," Proc. of SPIE, 2009, pp. 73970K-1 to 73970K-8, vol. 7397.

Stauth et al., "Self-assembled single-crystal silicon circuits on plastic," PNAS, Sep. 19, 2006, pp. 13922-13927, vol. 103, No. 38.

Yao, H. et al., "A contact lens with integrated telecommunication circuit and sensors for wireless and continuous tear glucose monitoring," J. Micromech. Microeng., 2012, pp. 1-10, vol. 22.

Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.

Yao et al., "A contact lens with embedded sensor for monitoring tear glucose level," Biosensors and Bioelectronics, 2011, pp. 3290-3296, vol. 26.

Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.

Yeager et al., "A 9 µA, Addressable Gen2 Sensor Tag for Biosignal Acquistion," IEEE Journal of Solid-State Circuits, Oct. 2010, pp. 2198-2209, vol. 45, No. 10.

Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

International Searching Authority, International Search Report and Written Opinion for PCT/US2013/069549 mailed Feb. 12, 2014, 9 pages.

Extended European Search Report issued in connection with co-pending European Patent Application No. 13871948.9, dated Aug. 14, 2015, European Patent Office, 8 pages.

\* cited by examiner

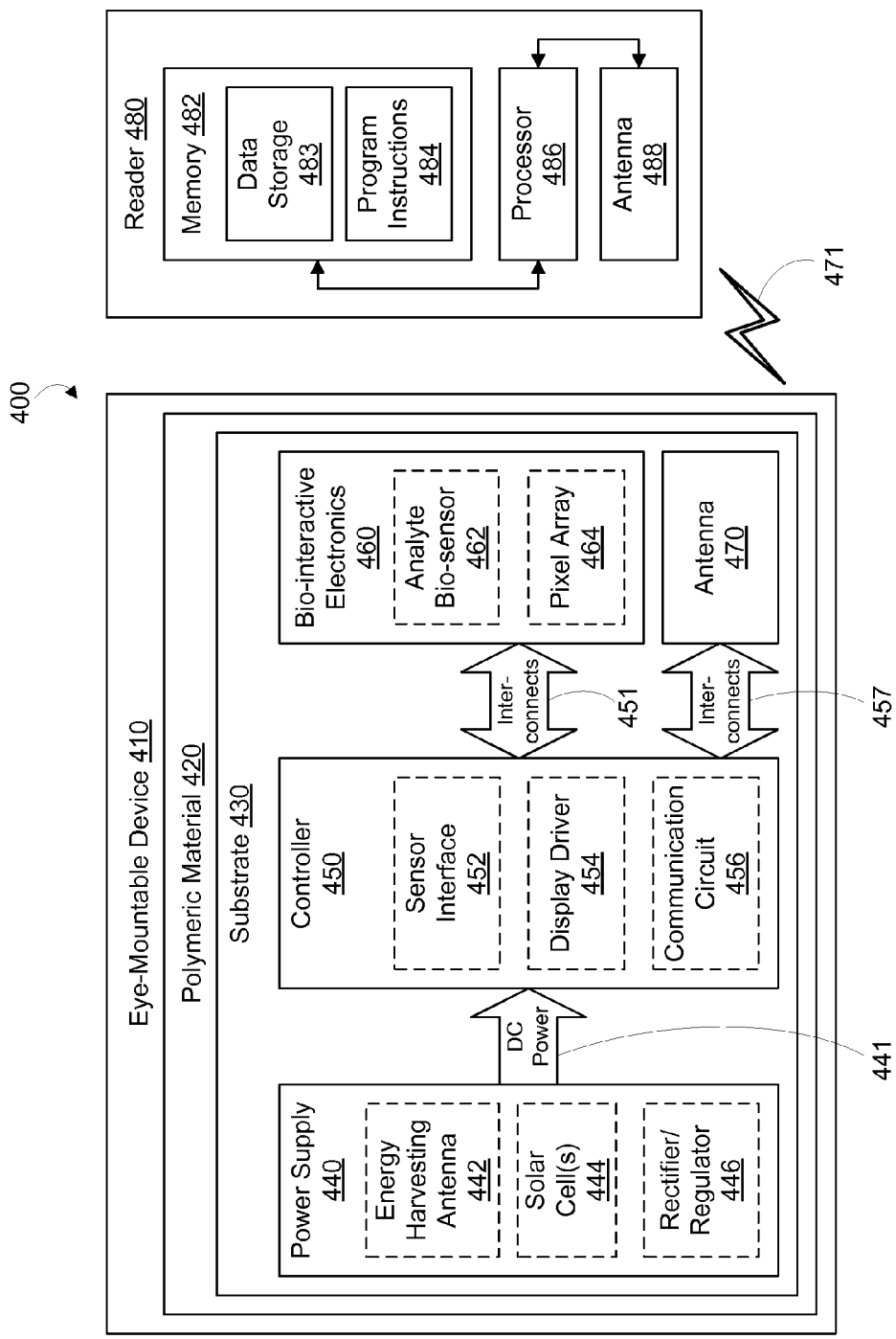

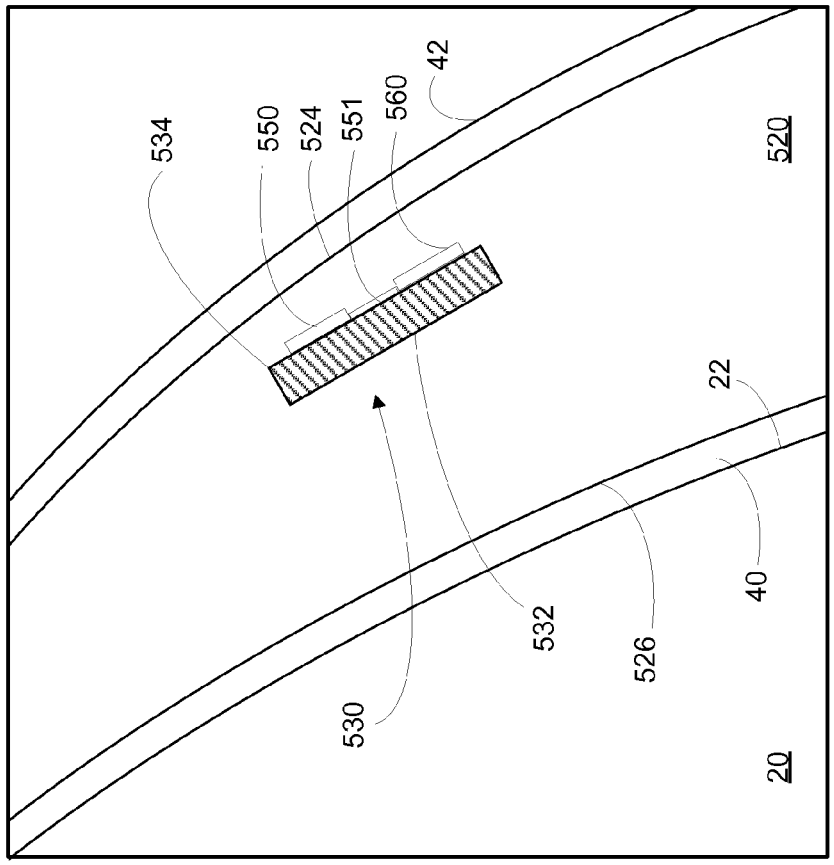
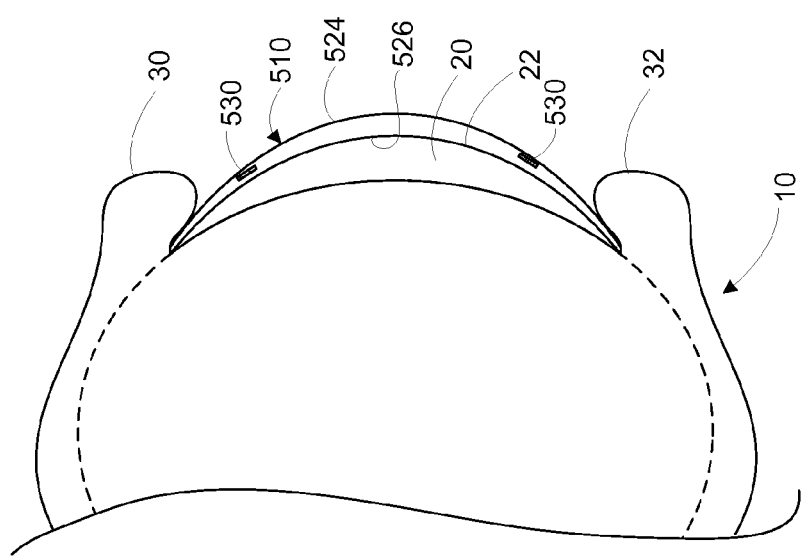

METHOD OF RING-SHAPED STRUCTURE PLACEMENT IN AN EYE-MOUNTABLE DEVICE

BACKGROUND

An eye-mountable device may be configured to monitor health-related information based on at least one analyte detected from an eye of a user wearing the eye-mountable device. Such an eye-mountable device may include a sensor apparatus configured to detect at least one analyte (e.g., glucose). For example, the eye-mountable device may be in the form of a contact lens that includes a sensor apparatus configured to detect the at least one analyte. The sensor apparatus may monitor health-related information of a user of the eye-mountable device, such as glucose level of the user. Further, the sensor apparatus may monitor various other types of health-related information.

SUMMARY

The present application discloses embodiments that relate to a method of ring-shaped structure placement in an eye-mountable device. In one aspect, the present application describes a method. The method may comprise applying a first amount of polymerizable material to a ring-shaped structure, where the ring-shaped structure comprises at least one sensor configured to detect an analyte. The method also may comprise positioning the ring-shaped structure with the first amount of polymerizable material applied thereto in a mold, where the mold is configured to form an eye-mountable device. The method also may comprise applying pressure on the ring-shaped structure in the mold while curing the first amount of polymerizable material. The method further may comprise adding a second amount of polymerizable material to the mold with the ring-shaped structure therein, and curing the second amount of polymerizable material to form an over-molded polymer layer such that the ring-shaped structure is at least partially enclosed in the eye-mountable device.

In another aspect, the present application describes a method. The method may comprise applying a first amount of polymerizable material to a ring-shaped structure, where the ring-shaped structure comprises at least one sensor configured to detect an analyte. The method also may comprise positioning the ring-shaped structure with the first amount of polymerizable material applied thereto on a previously-formed polymer layer in a mold, wherein the mold is configured to form an eye-mountable device. The method also may comprise applying, via a plunger comprising an elastic material, pressure on the ring-shaped structure in the mold. The method further may comprise adding a second amount of polymerizable material to the mold with the ring-shaped structure therein, and curing the second amount of polymerizable material to form an over-molded polymer layer such that the ring-shaped structure is fully enclosed in the eye-mountable device.

In still another aspect, the present application describes a method. The method may comprise applying an amount of adhesive material to a ring-shaped structure, where the ring-shaped structure comprises at least one sensor configured to detect an analyte. The method also may comprise positioning the ring-shaped structure with the amount of adhesive material applied thereto in a mold, where the mold is configured to form an eye-mountable device. The method also may comprise applying pressure on the ring-shaped structure in the mold while curing the amount of adhesive material. The method further may comprise adding a respective amount of polymerizable material to the mold with the ring-shaped structure therein, and curing the respective amount of polymerizable material to form an over-molded polymer layer such that the ring-shaped structure is at least partially enclosed in the eye-mountable device.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE FIGURES

FIG. 4 is a block diagram of a system with an eye-mountable device in wireless communication with an external reader, in accordance with an example embodiment.

FIG. 5C is a side cross-section view of the example eye-mountable device of FIGS. 5A and 5B while mounted to a corneal surface of an eye, in accordance with an example embodiment.

FIG. 5D is a side cross-section view showing the tear film layers surrounding the surfaces of the example eye-mountable device mounted as shown in FIG. 5C, in accordance with an example embodiment.

DETAILED DESCRIPTION

Figure 1:
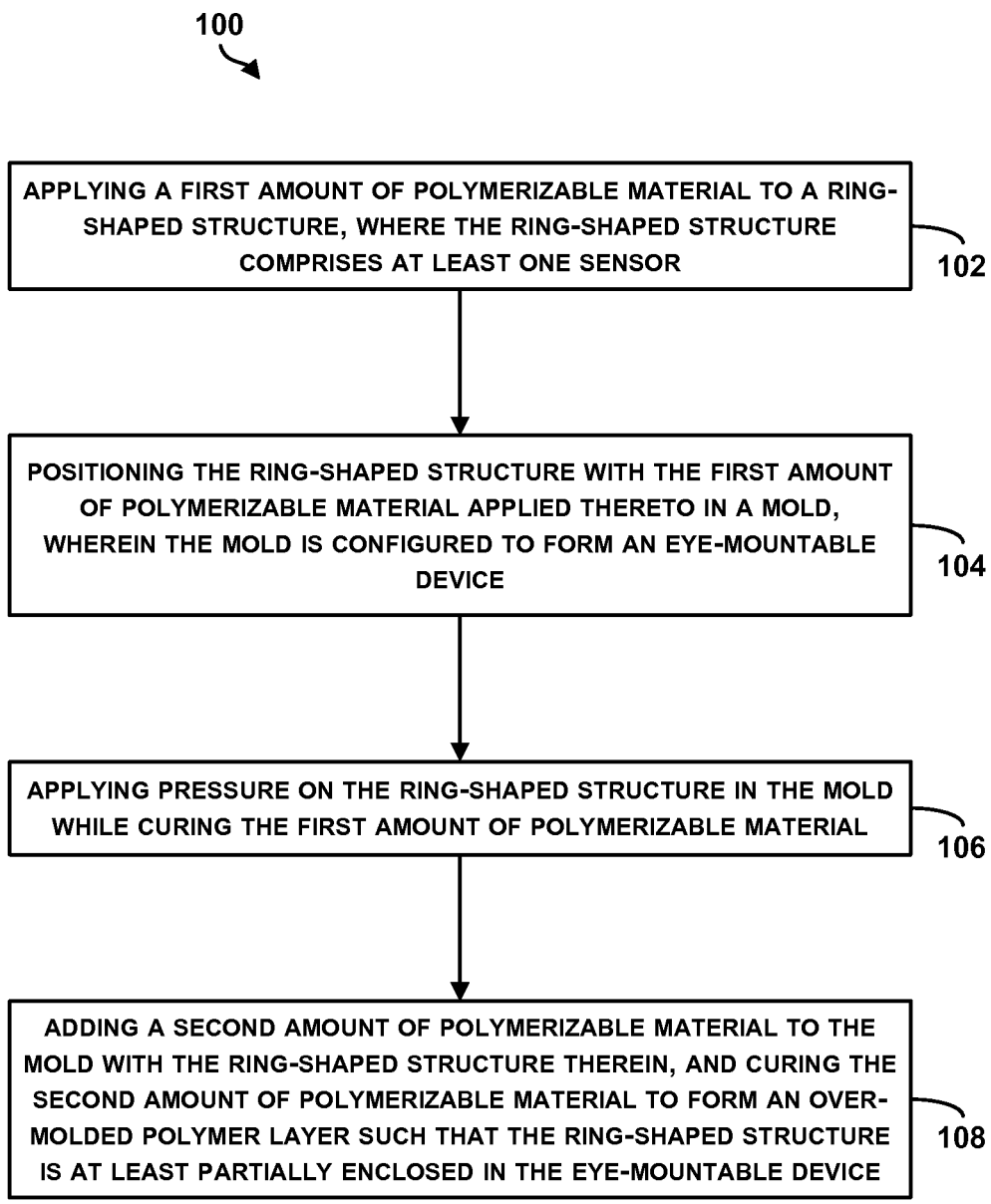
FIG. 1 is a flow chart illustrating a method of ring-shaped structure placement in an eye-mountable device, in accordance with an example embodiment.

The following detailed description describes various features and functions of the disclosed systems and methods with reference to the accompanying figures. In the figures, similar symbols identify similar components, unless context dictates otherwise. The illustrative system and method embodiments described herein are not meant to be limiting. It may be readily understood that certain aspects of the disclosed systems and methods can be arranged and combined in a wide variety of different configurations, all of which are contemplated herein.

I. Overview

An eye-mountable device (e.g., contact lens) may be configured to monitor health-related information, such as glucose level or corneal oxygen concentration, based on at least one analyte detected from an eye of a user wearing the eye-mountable device. Such an eye-mountable device may include a ring-shaped structure comprising at least one sensor configured to detect the at least one analyte. The present disclosure describes a method to place the ring-shaped structure in a desired location and apply pressure on the ring-shaped structure to fix the ring-shaped structure or portions of the ring-shaped structure to either an eye-mountable device mold or a previously-formed polymer layer.

In one example, small amounts of polymerizable material can be dispensed on the ring-shaped structure, and then the ring-shaped structure can be placed on the mold in the desired location. A plunger can then be used to apply pressure on the entire ring, and while the pressure is being applied, the polymerizable material can be cured. The plunger can then be removed and the rest of the eye-mountable device can be molded by addition and curing of more polymerizable material. In this embodiment, the ring-shaped structure may, at least partially, be enclosed by the eye-mountable device material.

In another example, small amounts of polymerizable material can be dispensed on the ring-shaped structure at discrete locations. The ring-shaped structure can be placed on the eye-mountable device mold in the desired location, and a plunger can then be used to apply pressure at the discrete locations. While the pressure is being applied, the polymerizable material may be cured. The plunger can then be removed and the rest of the eye-mountable device can be molded by addition and curing of more polymerizable material.

In still another example, small amounts of polymerizable material may be dispensed on the ring-shaped structure, and the ring-shaped structure can be placed on a pre-molded or previously-formed portion of the eye-mountable device with a defined thickness in the desired location. A plunger can then be used to apply pressure on the entire ring-shaped structure, or at discrete locations on the ring, and while the pressure is being applied, the polymerizable material can be cured. The plunger can then be removed and the rest of the eye-mountable device can be molded by addition and curing of more polymerizable material.

When pressure is applied to the entire ring-shaped structure to adhere the ring-shaped structure in place, the plunger may be referred to as a macroplunger. When the pressure is applied at the discrete locations of the ring-shaped structure, the plunger may be referred to as a microplunger. The plunger can be made of a compliant material such as a silicone elastomer or another elastic material, such that the plunger does not damage components on the ring-shaped structure.

Instead of or in addition to using small amount of polymerizable material as an adhesive to fix the ring-shaped structure in place, other methods can be used. For example, a polymer or other compound can be utilized that is melted and then the pressure is applied while the polymer is allowed to cool and harden. The ring-shaped structure is fixed in place when the polymer hardens. A thermosetting material can also be used as an adhesive. The thermosetting material may be in a molten state at high temperature, and in a solid or hardened state at lower temperatures.

In the example where the ring-shaped structure is placed on the pre-molded or previously-formed portion of the eye-mountable device, the method may involve a two-shot molding process. The first shot may involve forming a first polymer layer that defines an anterior (outward facing) side of the eye-mountable device. The first polymer layer may be formed by injecting a first shot of polymerizable material into a first molding cavity. After forming the first polymer layer, the ring-shaped structure may be placed on the first polymer layer. After the ring-shaped structure is placed on the first polymer layer and pressure is applied, a second polymer layer may be formed over the first polymer layer and the ring-shaped structure. After forming the second polymer layer, there will be polymer material on both sides of the ring-shaped structure such that the ring-shaped structure is fully enclosed by polymer materials. The second polymer layer may be formed by injecting a second shot of polymerizable material into a second molding cavity. The second polymer layer defines a posterior (inward facing) side of the eye-mountable device. However, in another example, forming the first polymer layer may involve forming the first polymer layer such that the first polymer layer defines the posterior side of the eye-mountable device, and forming the second polymer layer may involve forming the second polymer layer such that the second polymer layer defines the anterior side of the eye-mountable device. For instance, an example method for fabricating an eye-mountable device may involve: (i) forming a first polymer layer, where the first polymer layer defines a posterior side of the eye-mountable device; (ii) positioning a ring-shaped structure on the first polymer layer; and (iii) forming a second polymer layer over the first polymer layer and the ring-shaped structure, such that the ring-shaped structure is fully enclosed by the first polymer layer and the second polymer layer, where the second polymer layer defines an anterior side of the eye-mountable device and is configured to allow an analyte to diffuse therethrough. In this example, the at least one sensor may be oriented relative to the second polymer layer to receive the analyte via diffusion through the second polymer layer.

As used throughout this disclosure, the anterior side of the eye-mountable device refers to the outward-facing side of the eye-mountable device, whereas the posterior side of the eye-mountable device refers to the inward-facing side of the eye-mountable device. In particular, when the eye-mountable device is mounted on an eye of the user, the anterior side corresponds to the side of the eye-mountable device that is facing outward and thus not touching the eye of the user. Further, when the eye-mountable device is mounted on an eye of the user, the posterior side corresponds to the side of the eye-mountable device that is facing inward and thus touching the eye of the user.

II. Example Methods

FIG. 1 is a flow chart of a method 100 of ring-shaped structure placement in an eye-mountable device, in accordance with an example embodiment. The method 100 may include one or more operations, functions, or actions as illustrated by one or more of blocks 102-108. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

For purposes of illustration, the method 100 is described below as being carried out by a fabrication device that utilizes cast or compression molding. It should be understood, however, that the method 100 may be carried out by a fabrication device that utilizes other methods for forming the polymer layers.

At block 102, the method 100 includes applying a first amount of polymerizable material to a ring-shaped structure, where the ring-shaped structure comprises at least one sensor. In some examples, the ring-shaped structure (or ring-shaped substrate) may take the form of a full ring. In other examples, the ring-shaped ring may take the form of a partial ring, a segment of a ring, an annulus, or other geometries. In an example, small amounts (e.g., drops) of polymerizable material (e.g., a monomer or any type of adhesive) can be dispensed on substantially the entire ring-shaped structure. In another example, small amounts of polymerizable material can be dispensed on the ring-shaped structure at certain discrete locations. In some examples, instead of a polymerizable material, other adhesives can be used. For example, a thermosetting polymer can be used. The thermosetting polymer can be in a molten state at high temperature and may be allowed to harden when cooled.

At block 104, the method 100 includes positioning the ring-shaped structure with the first amount of polymerizable material applied thereto in a mold, where the mold is configured to form an eye-mountable device. In one example, the ring-shaped structure with the first amount of polymerizable material (or any other adhesive applied thereto) may be positioned directly on the mold. In another example, the ring-shaped structure with the first amount of polymerizable material may be positioned on a previously-formed polymer layer in the mold. The first amount of polymerizable material or adhesive may force the ring-shaped structure to conform to the geometry of the mold. In examples, the ring-shaped structure may be flat and need to be made to match the radius of curvature of the mold.

Figure 2A:
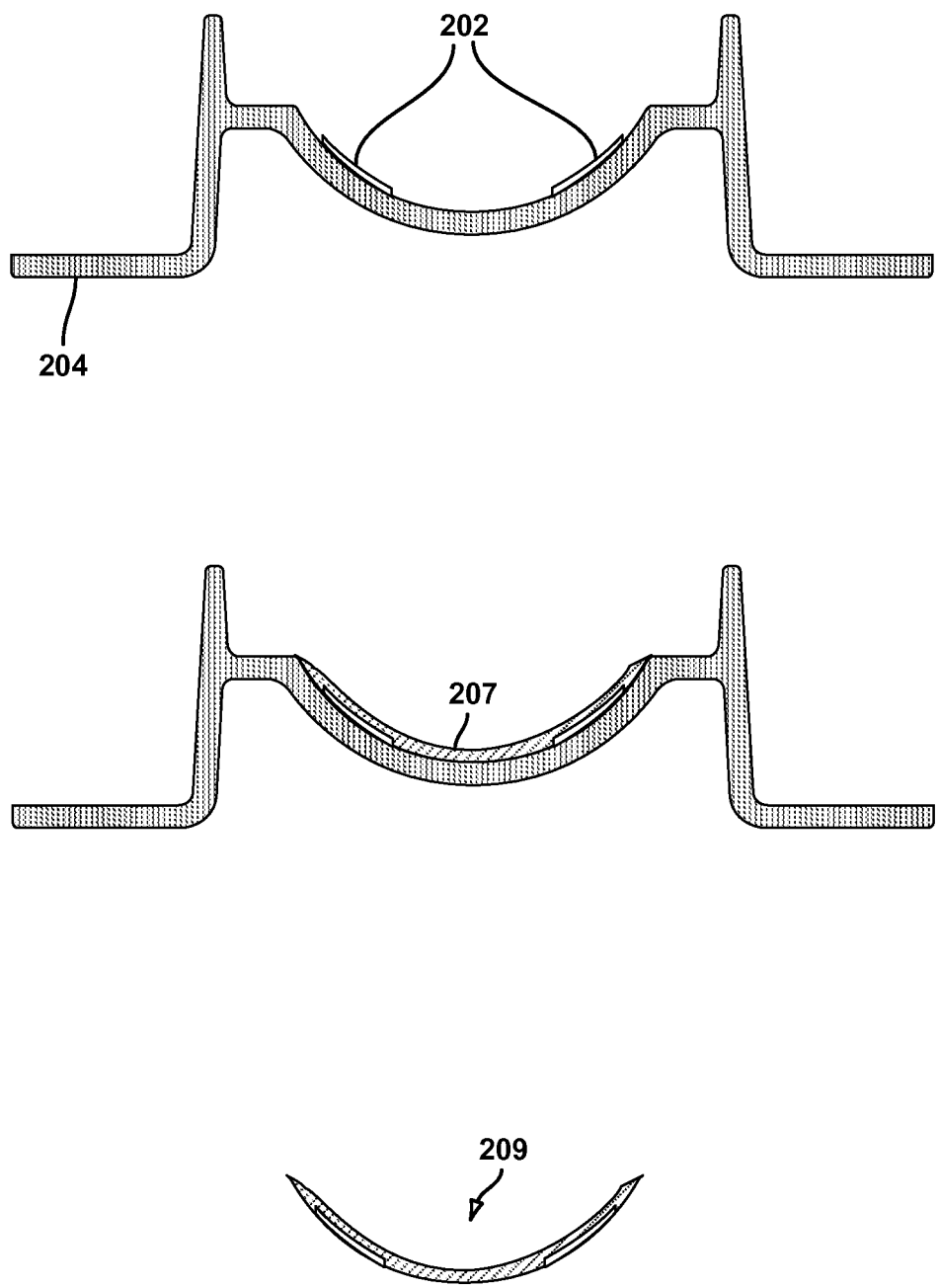
FIG. 2A illustrates a fabrication process of an eye-mountable device, in accordance with example embodiments.
Figure 2B:
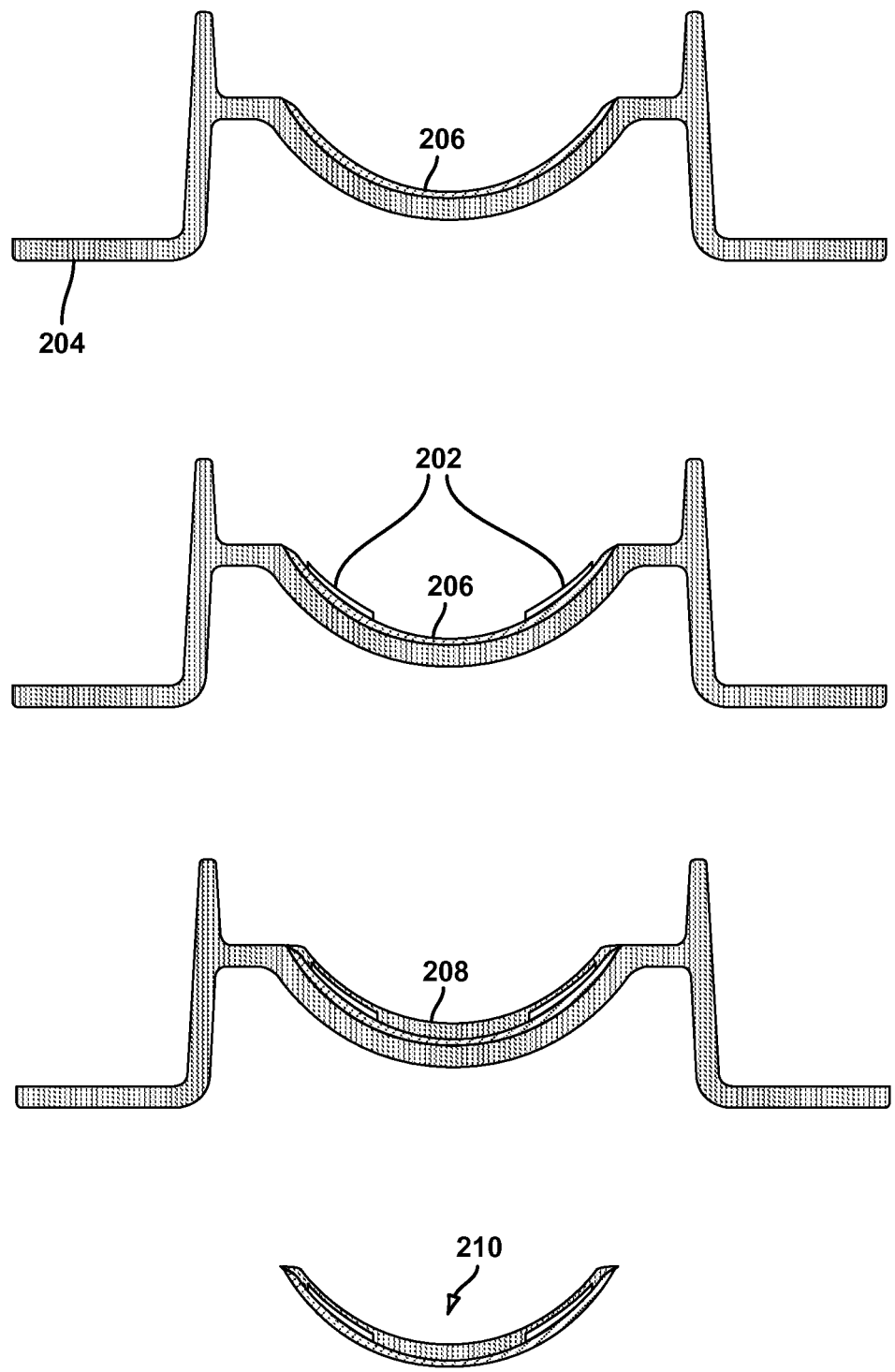
FIG. 2B illustrates an alternative fabrication process of an eye-mountable device, in accordance with example embodiments.

FIG. 2A illustrates a fabrication process of an eye-mountable device, in accordance with example embodiments. FIG. 2B illustrates an alternative fabrication process of an eye-mountable device, in accordance with example embodiments. In FIG. 2A, a ring-shaped structure 202 is directly adhered to an anterior mold 204 of a fabrication device that can be used to implement the method 100. In FIG. 2B, a first or previously-formed polymer layer 206 of polymerizable material is in place in the anterior mold 204, and the ring-shaped structure 202 is positioned on or adhered to the previously-formed polymer layer 206.

Figure 3A:
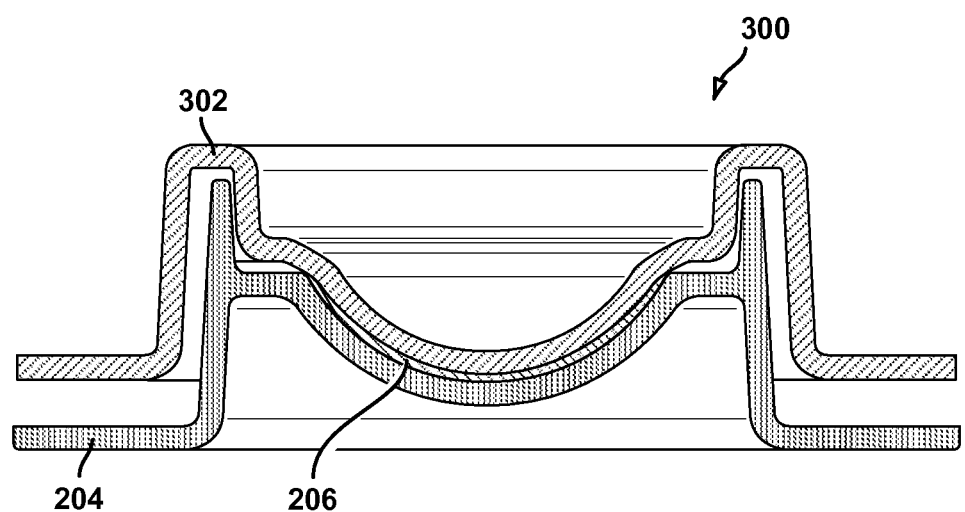
FIG. 3A illustrates formation of a first polymer layer, in accordance with an example embodiment.

FIG. 3A illustrates a fabrication device 300 and formation of a first (previously-formed) layer 206, in accordance with an example embodiment. A first molding cavity of the anterior mold 204 may be filled with polymer material, and the polymer material may be compressed into a polymer layer (i.e., the previously-formed polymer layer 206) by a second molding cavity of a mold 302. The previously-formed polymer layer 206 may define an anterior side of an eye-mountable device. The anterior side defines the side that is not touching the eye of the user of the eye-mountable device.

The first or previously-formed polymer layer 206 may be formed with a thickness that allows an analyte to diffuse therethrough. The first and second molding cavities may be configured to achieve a given desired thickness of the previously-formed polymer layer 206. For instance, the previously-formed polymer layer 206 may have a thickness of less than 50 micrometers. Typically, as a polymer layer becomes thicker, the polymer layer allows for less diffusion through the layer. As an example, diffusion of a given analyte is typically greater through a 25 micrometer polymer layer than through a 100 micrometer or thicker polymer layer. For at least some types of analyte, a polymer layer having a thickness of less than 50 micrometers can allow for a sufficient amount of analyte to diffuse therethrough in order for the eye-mountable device to perform health-related measurements. In general, however, the thickness of the polymer layer through which the analyte diffuses to reach the sensor for measurement can be selected based on the type of analyte, the type of polymer, the type of sensor, and/or other considerations. In an example, the thickness of the previously-formed polymer layer 206 may be selected based on the particular analyte or analytes the eye-mountable device is configured to detect. For example, an optimal thickness for a first analyte may be 10 micrometers, while an optimal thickness for a second analyte may be 25 micrometers. Other examples are possible as well.

In an example, the polymer of the previously-formed polymer layer 206 may be any material that can form an eye-compatible polymer layer. For example, the polymer of the previously-formed polymer layer 206 may be a formulation containing polymerizable monomers known to form hydrogels, silicone hydrogels, silicone elastomers, and rigid gas permeable materials. Further, the polymer may form a transparent or substantially transparent polymer layer. As such, the use of such polymer in the previously-formed polymer layer 206 may result in an eye-mountable device through which the wearer can see when mounted on the wearer's eye. In an example, the polymer is a hydrogel material, such as silicone hydrogel. Other materials are possible as well. The ring-shaped structure 202 may be more rigid than the polymer material used to form the eye-mountable device.

Although FIG. 3A illustrates forming the previously-formed polymer layer 206 through cast molding, other methods for forming the previously-formed polymer layer 206 are possible as well. For example, the previously-formed polymer layer 206 may be formed via injection molding. In injection molding, rather than the polymer material being compressed between molding cavities, molding material may heated and injected or otherwise forced into a molding cavity or cavities. The injected molding material may then cool and harden to the configuration of the molding cavity or cavities.

As another example, the previously-formed polymer layer 206 may be formed via spin casting. Through spin-casting techniques, a respective fabrication device may form a polymer layer of a precise thickness. In an example, a spin-casting mold may be spun along its central access at a set speed, and the polymer may be introduced to the mold as the mold is spinning in order to form the previously-formed polymer layer 206. The final thickness of the previously-formed polymer layer 206 may be influenced by various factors, including but not limited to the spin-casting mold, the amount of polymer introduced to the spin-casting mold, properties of the polymer such as viscosity, and/or the speed at which the spin-casting mold is rotated. These factors may be varied in order to result in a polymer layer of a well-defined thickness.

Figure 3B:
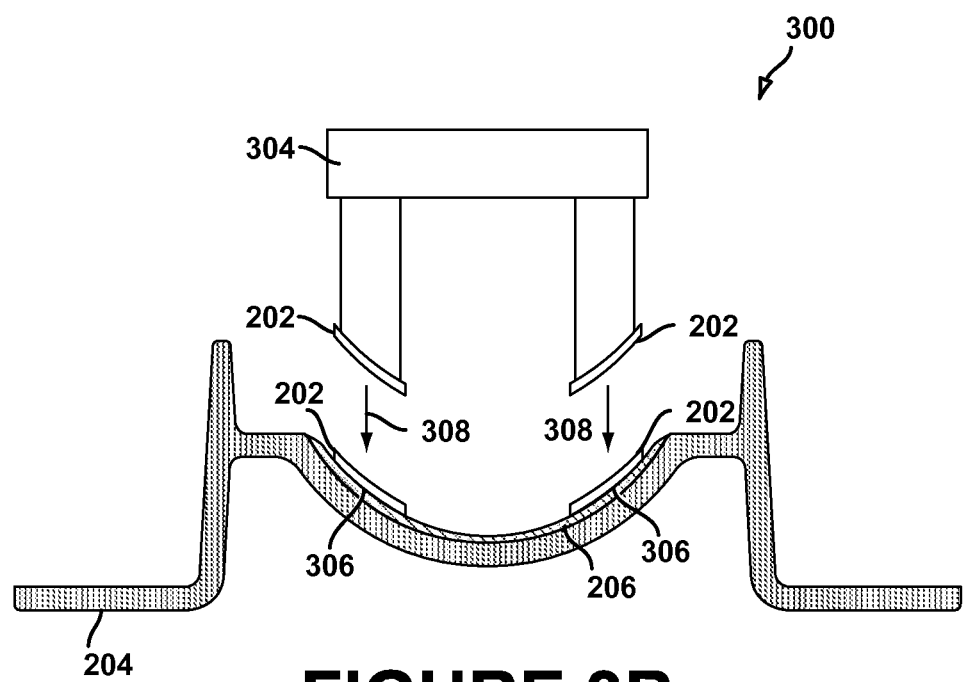
FIG. 3B illustrates positioning of the ring-shaped structure on a first polymer layer, in accordance with an example embodiment.

FIG. 3B illustrates an example positioning of the ring-shaped structure 202 on a first polymer layer 206, in accordance with an example embodiment. Although FIG. 3B illustrates positioning the ring-shaped structure 202 on the previously-formed polymer layer 206 as shown in FIG. 2B, a similar process can be used to position the ring-shaped structure 202 directly on the anterior mold 204 as shown in FIG. 2A. As shown in FIG. 3B, the fabrication device 300 includes a positioning apparatus 304 that may be configured to position the ring-shaped structure at a desired location on the previously-formed polymer layer 206.

In an example, the positioning apparatus 304 may be a robotic system configured to place the ring-shaped structure 202 at a defined location 306 on the previously-formed polymer layer 206. For instance, the robotic system may (i) pick up the ring-shaped structure 202 (e.g., via suction), (ii) position the ring-shaped structure 202 above the previously-formed polymer layer 206, and then (iii) lower the ring-shaped structure 202 toward the previously-formed polymer layer 206, as shown by arrows 308. When the ring-shaped structure 202 is positioned in the desired location 306 on the previously-formed polymer layer 206, the positioning apparatus 304 may then release the ring-shaped structure 202 (e.g., by releasing the suction).

In an example, the positioning apparatus 304 may include a vision system configured to assist with the placement of the ring-shaped structure 202. Such a vision system may facilitate guiding the ring-shaped structure 202 to a precise location on the anterior mold 204 or the previously-formed polymer layer 206. In an example, a vision system may be appropriate for situations in which the production specifications for the eye-mountable device have requirements with low tolerances related to the positioning of the ring-shaped structure 202 within the eye-mountable device.

Referring back to FIG. 1, at block 106, the method 100 includes applying pressure on the ring-shaped structure in the mold while curing the first amount of polymerizable material. Referring to FIGS. 2A-2B, whether the ring-shaped structure 202 and the first amount of polymerizable material (adhesive) applied thereto is positioned directly in the anterior mold 204 or positioned on the previously-formed polymer layer 206, pressure can be applied on the ring-shaped structure 202 while curing the first amount of polymerizable material. Applying pressure while curing the first amount of polymerizable material facilitates adhering or fixing the ring-shaped structure 202 in place. As described above at block 102, the first amount of polymerizable material, or any adhesive material, can be a small amount that is dispensed on substantially the entire ring-shaped structure 202 or dispensed at discrete locations on the ring-shaped structure 202.

In one example, the adhesive material can be dispensed as droplets that are injected on the ring-shaped structure 202. In another example, a brush can be dipped in the adhesive material and then applied to the ring-shaped structure 202. In still another example, an air spray nebulizer can be used to atomize the adhesive material and apply a uniform layer of the adhesive material to the ring-shaped structure 202. Other methods are also possible.

Figure 3C:
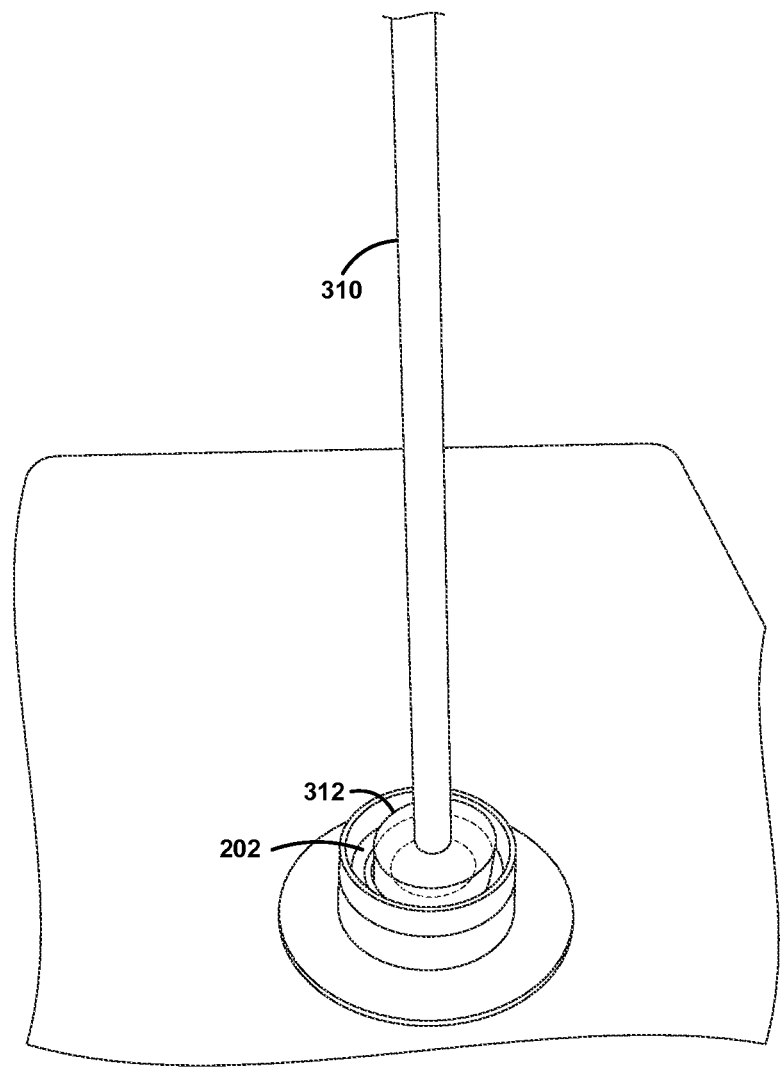
FIG. 3C illustrates applying pressure on an entire ring-shaped structure, in accordance with an example embodiment.

In the example where the first amount of polymerizable material is applied to the entire ring-shaped structure 202, a plunger can be used to apply pressure on the entire ring-shaped structure 202. FIG. 3C illustrates applying pressure on the entire ring-shaped structure 202, in accordance with an example embodiment. When pressure is applied to the entire ring-shaped structure 202 to adhere it in place, the plunger may be referred to as a macroplunger. FIG. 3C illustrates an example macroplunger 310 applying pressure on the entire ring-shaped structure 202 to adhere the ring-shaped structure 202 to the anterior mold 204 or the previously-formed polymer layer 206. In examples, the plunger 310 or the end of the plunger 310 can be made of a compliant material 312 (e.g., soft, flexible, or elastic) such as a silicone elastomer or another elastic material, such that the plunger may not damage components on the ring-shaped structure.

Figure 3D:
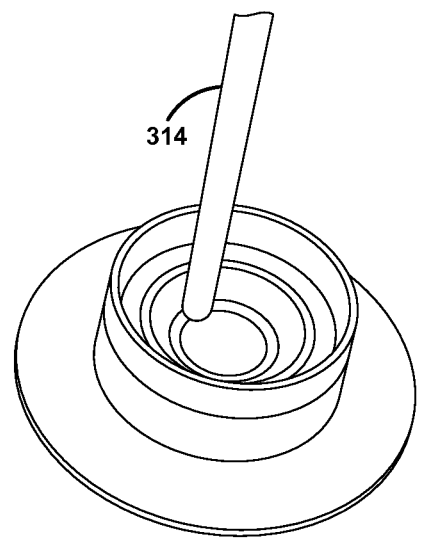
FIG. 3D illustrates applying pressure at a discrete location on a ring-shaped structure, in accordance with an example embodiment.
Figure 3E:
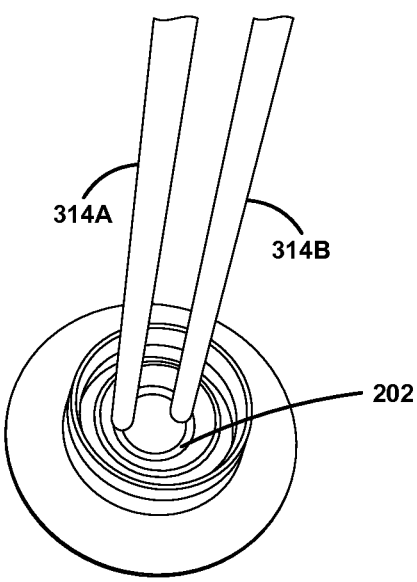
FIG. 3E illustrates applying pressure at multiple discrete locations on a ring-shaped structure, in accordance with an example embodiment.

Alternatively, in the example where the first amount of polymerizable material is applied at discrete locations on the ring-shaped structure 202, a plunger can be used to apply pressure at the discrete locations. FIGS. 3D and 3E illustrate applying pressure at discrete locations on the ring-shaped structure 202, in accordance with an example embodiment. When the pressure is applied to just the discrete locations of the ring-shaped structure 202, the plunger may be referred to as a microplunger. FIG. 3D illustrates a microplunger 314 applying pressure at a discrete location on the ring-shaped structure 202. The microplunger 314 can be raised and lowered again at a different discrete location on the ring-shaped structure 202 such that pressure may be applied at the different discrete locations in a sequential manner. Alternatively, FIG. 3E illustrates multiple plungers, such as plungers 314A and 314B, can be used to apply pressure at the discrete locations at substantially the same time.

In some examples, applying pressure on the ring-shaped structure 202 can be accomplished using the positioning apparatus 304 illustrated in FIG. 3B after positioning the ring-shaped structure 202 on the anterior mold 204 or the previously-formed polymer layer 206.

The first amount of polymerizable material (or any type of adhesive) can be cured while pressure is being applied. Curing involves the hardening of a polymer material by cross-linking of polymer chains, and curing may be, for example, brought about by chemical additives, ultraviolet radiation, electron beam, and/or heat. In an example, the polymerizable material may be made of a light-curable polymer material that can be cured using ultraviolet (UV) light or visible light. In addition to light curing, other methods of curing are possible as well, such as chemical additives and/or heat.

In the example where the ring-shaped structure 202 is positioned on the previously-formed polymer layer 206, the previously-formed polymer layer 206 can be cured to a partially-cured state before positioning the ring-shaped structure 202. The partially-cured state may, for example, be approximately 50-75% of a fully cured state. Other partially-cured states are possible as well. By partially curing the previously-formed polymer layer 206 to a partially-cured state, the previously-formed polymer layer 206 may have a tackiness that facilitates adhesion thereto. Such tackiness may ensure that the ring-shaped structure 202 placed on the previously-formed polymer layer 206 remains securely fixed in a given location throughout the formation of the eye-mountable device.

Instead of or in addition to using the first amount (e.g., small amount or drops) of polymerizable material as an adhesive to fix the ring-shaped structure 202 in place, other methods can be used. For example, a thermosetting polymer or other materials can be melted and then the pressure is applied while the molten material is allowed to cool and harden. After the material hardens, the ring-shaped structure 202 will be fixed in place.

Referring back to FIG. 1, at block 108, the method 100 includes adding a second amount of polymerizable material to the mold with the ring-shaped structure therein, and curing the second amount of polymerizable material to form an over-molded polymer layer such that the ring-shaped structure is at least partially enclosed in the eye-mountable device. The first amount of polymerizable material (or any adhesive) may keep the ring-shaped structure in a fixed geometry while the second amount of polymerizable material is cured around the ring-shaped structure. Referring to FIG. 2A, where the ring-shaped structure 202 is directly positioned on the anterior mold 204, a second amount of polymerizable material can be added above the positioned ring-shaped structure 202 to form a polymer layer 207. The polymer layer 207 can be cured and hardened such that the ring-shaped structure 202 is adhered to the polymer layer 207. The polymer layer 207 and the ring-shaped structure 202 can then be removed from the mold 204 to obtain the eye-mountable device 209 where the ring-shaped structure 202 is at least partially enclosed in the eye-mountable device 209. For example, a portion of the ring-shaped structure may be exposed at the anterior side and/or posterior side of the eye-mountable device.

Alternatively, in FIG. 2B, the second amount of polymerizable material is added after the ring-shaped structure 202 is positioned on the previously-formed polymer layer 206 to form the polymer layer 208. In this case, the previously-formed polymer layer 206 may be referred to as the first polymer layer, and the polymer layer 208 may be referred to as the second polymer layer. The previously-formed (first) polymer layer 206, the second polymer layer 208, and the ring-shaped structure 202 embedded therein can then be removed from the mold 204 to obtain the eye-mountable device 210. In this example, the ring-shaped structure 202 can be fully enclosed in the eye-mountable device 210.

Figure 3F:
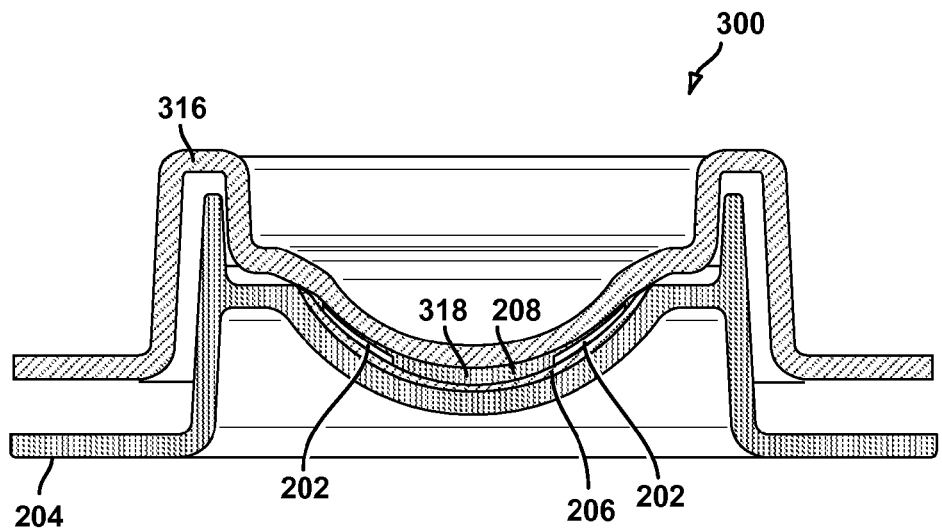
FIG. 3F illustrates formation of a second polymer layer over the first polymer layer and the ring-shaped structure, in accordance with an example embodiment.

FIG. 3F illustrates formation of the second polymer layer 208 over the previously-formed polymer layer 206 and the ring-shaped structure 202, in accordance with an example embodiment. FIG. 3F illustrates an example third molding cavity of a posterior mold 316. The third molding cavity may define the posterior side of the eye-mountable device. In particular, the curvature of the posterior side may be defined by the third molding cavity of the posterior mold 316. Further, the molding cavities of the anterior mold 204 and posterior mold 316 may be configured to control the thickness of the layer formed between the two cavities.

With reference to FIG. 3F, the first molding cavity of the anterior mold 204, which already holds the previously-formed polymer layer 206 to which the ring-shaped structure 202 is adhered, may be filled with the second amount of polymerizable material 318. This polymer material 318 may be formed into the second polymer layer 208 by the compression between the first molding cavity of the anterior mold 204 and the third molding cavity of the posterior mold 316. As a result, the second polymer layer 208 may over-mold the ring-shaped structure 202, such that the ring-shaped structure 202 is fully enclosed by the previously-formed polymer layer 206 and the second polymer layer 208.

Figure 3G:
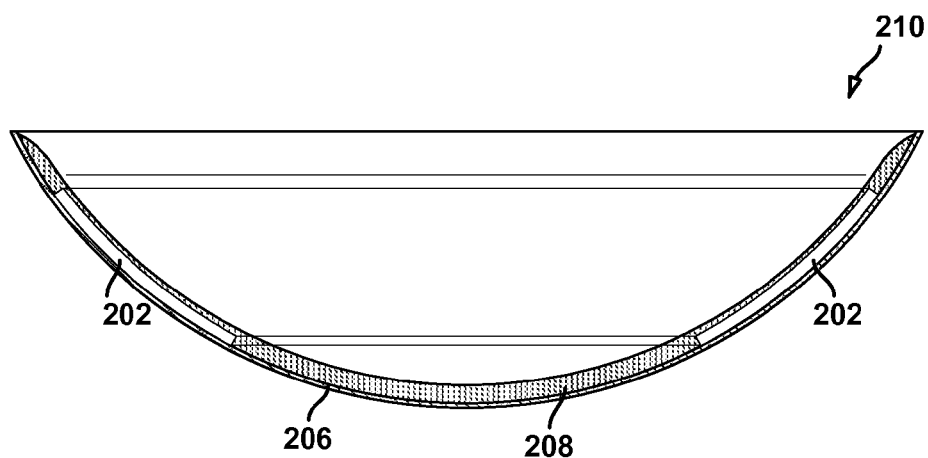
FIG. 3G illustrates an example eye-mountable device, in accordance with an example embodiment.

In examples, after the second polymer layer 208 is formed, the second amount of polymerizable material 318 may be cured. FIG. 3G illustrates the eye-mountable device 210, in accordance with an example embodiment. FIG. 3G depicts a perspective cross-section of the eye-mountable device 210 after the eye-mountable device 210 is removed from the fabrication device 300.

FIG. 3G shows the anterior side defined by the previously-formed polymer layer 206 as a thin layer, while the second polymer layer 208 is a thicker layer. In an example, the maximum thickness of the final device may range from 100-500 micrometers. Further, in such an example, the thin previously-formed polymer layer 206 may be less than 50 micrometers, while the thicker second polymer layer 208 may have a maximum thickness of between 100 and 500 micrometers. In other examples, the previously-formed polymer layer 206 and second polymer layer 208 may each have a larger or smaller thickness.

In an example, the second polymer layer 208 may be composed of the same polymer material as the previously-formed polymer layer 206. However, in other examples, the second polymer layer 208 may be composed of a different polymer material than the previously-formed polymer layer 206.

III. Example Systems and Devices

As mentioned above, an eye-mountable device may be fabricated using the example methods described above. Further, this eye-mountable device may be configured to monitor health-related information based on at least one analyte detected from an eye of a user wearing the eye-mountable device. An example eye-mountable device configured to monitor health-related information based on at least one analyte detected from an eye of a user is described in greater detail below with reference to FIGS. 4 and 5A-5D.

A ring-shaped structure in accordance with an exemplary embodiment may include a sensor, control electronics and an antenna all situated on a substrate. The control electronics may operate the sensor to perform readings and operate the antenna to wirelessly communicate the readings from the sensor to an external reader via the antenna. The sensor can be arranged on the substrate to face outward, away from the corneal surface of the user, so as to generate clinically relevant readings from tear fluid of the user that diffuses through the anterior side of the eye-mountable device. For example, the ring-shaped structure can be suspended in the lens material and situated such that the sensor is less than 10 micrometers from the anterior edge of the eye-mountable device. In another example, the ring-shaped structure may be partially-enclosed in the lens material such that part of the ring-shaped structure is not encapsulated in the lens material and is directly exposed to tear fluid. In still another example, the sensor can be arranged on the substrate to face inward, toward the corneal surface, so as to generate clinically relevant readings from near the surface of the cornea and/or from tear fluid interposed between the contact lens and the corneal surface. The sensor can generate an output signal indicative of a concentration of an analyte that diffuses through the lens material to the embedded sensor.

FIG. 4 is a block diagram of a system 400 with an eye-mountable device 410 in wireless communication with an external reader 480. The exposed regions of the eye-mountable device 410 are made of a polymeric material 420 formed to be contact-mounted to a corneal surface of an eye. In accordance with the exemplary methods, polymeric material 420 may comprise a first polymer layer and a second polymer layer.

The ring-shaped structure may comprise a substrate, such as substrate 430 that is embedded in the polymeric material 420 to provide a mounting surface for a power supply 440, a controller 450, bio-interactive electronics 460, and a communication antenna 470. The bio-interactive electronics 460 are operated by the controller 450. The power supply 440 supplies operating voltages to the controller 450 and/or the bio-interactive electronics 460. The antenna 470 is operated by the controller 450 to communicate information to and/or from the eye-mountable device 410. The antenna 470, the controller 450, the power supply 440, and the bio-interactive electronics 460 can all be situated on the embedded substrate 430. Because the eye-mountable device 410 includes electronics and is configured to be contact-mounted to an eye, it may also be referred to as an ophthalmic electronics platform.

To facilitate contact-mounting, the polymeric material 420 can have a concave surface configured to adhere ("mount") to a moistened corneal surface (e.g., by capillary forces with a tear film coating the corneal surface). Additionally or alternatively, the eye-mountable device 410 can be adhered by a vacuum force between the corneal surface and the polymeric material 420 due to the concave curvature. While mounted with the concave surface against the eye, the anterior or outward-facing surface of the polymeric material 420 can have a convex curvature that is formed to not interfere with eye-lid motion while the eye-mountable device 410 is mounted to the eye. For example, the polymeric material 420 can be a substantially transparent curved polymeric disk shaped similarly to a contact lens.

The polymeric material 420 can include one or more biocompatible materials, such as those employed for use in contact lenses or other ophthalmic applications involving direct contact with the corneal surface. The polymeric material 420 can optionally be formed in part from such biocompatible materials or can include an outer coating with such biocompatible materials. The polymeric material 420 can include materials configured to moisturize the corneal surface, such as hydrogels and the like. In some instances, the polymeric material 420 can be a deformable ("non-rigid") material to enhance wearer comfort. In some instances, the polymeric material 420 can be shaped to provide a predetermined, vision-correcting optical power, such as can be provided by a contact lens.

The substrate 430 includes one or more surfaces suitable for mounting the bio-interactive electronics 460, the controller 450, the power supply 440, and the antenna 470. The substrate 430 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) can be patterned on the substrate 430 to form circuitry, electrodes, etc. For example, the antenna 470 can be formed by depositing a pattern of gold or another conductive material on the substrate 430. Similarly, interconnects 451, 457 between the controller 450 and the bio-interactive electronics 460, and between the controller 450 and the antenna 470, respectively, can be formed by depositing suitable patterns of conductive materials on the substrate 430. A combination of resists, masks, and deposition techniques can be employed to pattern materials on the substrate 430.

The substrate 430 can be a relatively rigid material, such as polyethylene terephthalate ("PET") or another material sufficient to structurally support the circuitry and/or electronics within the polymeric material 420. The eye-mountable device 410 can alternatively be arranged with a group of unconnected substrates rather than a single substrate. For example, the controller 450 and a bio-sensor or other bio-interactive electronic component can be mounted to one substrate, while the antenna 470 is mounted to another substrate and the two can be electrically connected via the interconnects 457.

In some embodiments, the bio-interactive electronics 460 (and the substrate 430) can be positioned away from the center of the eye-mountable device 410 and thereby avoid interference with light transmission to the eye through the center of the eye-mountable device 410. For example, where the eye-mountable device 410 is shaped as a concave-curved disk, the substrate 430 can be embedded around the periphery (e.g., near the outer circumference) of the disk. In some embodiments, the bio-interactive electronics 460 (and the substrate 430) can be positioned in the center region of the eye-mountable device 410. The bio-interactive electronics 460 and/or substrate 430 can be substantially transparent to incoming visible light to mitigate interference with light transmission to the eye. Moreover, in some embodiments, the bio-interactive electronics 460 can include a pixel array 464 that emits and/or transmits light to be perceived by the eye according to display driver instructions. Thus, the bio-interactive electronics 460 can optionally be positioned in the center of the eye-mountable device so as to generate perceivable visual cues to a wearer of the eye-mountable device 410, such as by displaying information via the pixel array 464.

The substrate 430 can be shaped as a flattened ring with a radial width dimension sufficient to provide a mounting platform for the embedded electronics components. The substrate 430 can have a thickness sufficiently small to allow the substrate 430 to be embedded in the polymeric material 420 without influencing the profile of the eye-mountable device 410. The substrate 430 can have a thickness sufficiently large to provide structural stability suitable for supporting the electronics mounted thereon. For example, the substrate 430 can be shaped as a ring-shaped structure with a diameter of about 10 millimeters, a radial width of about 1 millimeter (e.g., an outer radius 1 millimeter larger than an inner radius), and a thickness of about 50 micrometers. The substrate 430 can optionally be aligned with the curvature of the anterior side of the eye-mountable device.

The power supply 440 is configured to harvest ambient energy to power the controller 450 and bio-interactive electronics 460. For example, a radio-frequency energy-harvesting antenna 442 can capture energy from incident radio radiation. Additionally or alternatively, solar cell(s) 444 ("photovoltaic cells") can capture energy from incoming ultraviolet, visible, and/or infrared radiation. Furthermore, an inertial power scavenging system can be included to capture energy from ambient vibrations. The energy harvesting antenna 442 can optionally be a dual-purpose antenna that is also used to communicate information to the external reader 480. That is, the functions of the communication antenna 470 and the energy harvesting antenna 442 can be accomplished with the same physical antenna.

A rectifier/regulator 446 can be used to condition the captured energy to a stable DC supply voltage 441 that is supplied to the controller 450. For example, the energy harvesting antenna 442 can receive incident radio frequency radiation. Varying electrical signals on the leads of the antenna 442 are output to the rectifier/regulator 446. The rectifier/regulator 446 rectifies the varying electrical signals to a DC voltage and regulates the rectified DC voltage to a level suitable for operating the controller 450. Additionally or alternatively, output voltage from the solar cell(s) 444 can be regulated to a level suitable for operating the controller 450. The rectifier/regulator 446 can include one or more energy storage devices arranged to mitigate high frequency variations in the ambient energy gathering antenna 442 and/or solar cell(s) 444. For example, an energy storage device (e.g., capacitor, inductor, etc.) can be connected to the output of the rectifier 446 so as to function as a low-pass filter.

The controller 450 is turned on when the DC supply voltage 441 is provided to the controller 450, and the logic in the controller 450 operates the bio-interactive electronics 460 and the antenna 470. The controller 450 can include logic circuitry configured to operate the bio-interactive electronics 460 so as to interact with a biological environment of the eye-mountable device 410. The interaction could involve the use of one or more components, such as an analyte bio-sensor 462, in bio-interactive electronics 460 to obtain input from the biological environment. Alternatively or additionally, the interaction could involve the use of one or more components, such as pixel array 464, to provide an output to the biological environment.

In one example, a sensor interface module 452 can be included for operating the analyte bio-sensor 462. The analyte bio-sensor 462 can be, for example, an amperometric electrochemical sensor that includes a working electrode and a reference electrode. Application of an appropriate voltage between the working and reference electrodes can cause an analyte to undergo electrochemical reactions (e.g., reduction and/or oxidation reactions) at the working electrode to generate an amperometric current. The amperometric current can be dependent on the analyte concentration, and thus the amount of amperometric current can provide an indication of analyte concentration. In some embodiments, the sensor interface module 452 can be a potentiostat configured to apply a voltage difference between the working and reference electrodes while measuring a current through the working electrode.

In some instances, a reagent can also be included to sensitize the electrochemical sensor to desired analytes. For example, a layer of glucose oxidase ("GOD") can be situated around the working electrode to catalyze glucose into hydrogen peroxide ($H_2O_2$). The hydrogen peroxide can then be oxidized at the working electrode, which releases electrons to the working electrode, which generates a current.

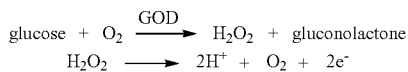

$$\text{glucose} + O_2 \xrightarrow{\text{GOD}} H_2O_2 + \text{gluconolactone}$$
$$H_2O_2 \longrightarrow 2H^+ + O_2 + 2e^-$$

The current generated by either reduction or oxidation reactions is approximately proportionate to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportionate to the concentration of the analyte molecules. The current thus provides an indication of the analyte concentration.

The controller 450 can optionally include a display driver module 454 for operating a pixel array 464. The pixel array 464 can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 454. Such a pixel array 464 can also optionally include more than one color of pixels (e.g., red, green, and blue pixels) to render visual content in color. The display driver module 454 can include, for example, one or more data lines providing programming information to the separately programmed pixels in the pixel array 464 and one or more addressing lines for setting groups of pixels to receive such programming information. Such a pixel array 464 situated on the eye can also include one or more lenses to direct light from the pixel array 464 to a focal plane perceivable by the eye.

The controller 450 can also include a communication circuit 456 for sending and/or receiving information via the antenna 470. The communication circuit 456 can optionally include one or more oscillators, mixers, frequency injectors, etc. to modulate and/or demodulate information on a carrier frequency to be transmitted and/or received by the antenna 470. In some examples, the eye-mountable device 410 is configured to indicate an output from a bio-sensor by modulating an impedance of the antenna 470 in a manner that is perceivably by the external reader 480. For example, the communication circuit 456 can cause variations in the amplitude, phase, and/or frequency of backscatter radiation from the antenna 470, and such variations can be detected by the reader 480.

The controller 450 is connected to the bio-interactive electronics 460 via interconnects 451. For example, where the controller 450 includes logic elements implemented in an integrated circuit to form the sensor interface module 452 and/or display driver module 454, a patterned conductive material (e.g., gold, platinum, palladium, titanium, copper, aluminum, silver, metals, combinations of these, etc.) can connect a terminal on the chip to the bio-interactive electronics 460. Similarly, the controller 450 is connected to the antenna 470 via interconnects 457.

It is noted that the block diagram shown in FIG. 4 is described in connection with functional modules for convenience in description. However, embodiments of the eye-mountable device 410 can be arranged with one or more of the functional modules ("sub-systems") implemented in a single chip, integrated circuit, and/or physical feature. For example, while the rectifier/regulator 446 is illustrated in the power supply block 440, the rectifier/regulator 446 can be implemented in a chip that also includes the logic elements of the controller 450 and/or other features of the embedded electronics in the eye-mountable device 410. Thus, the DC supply voltage 441 that is provided to the controller 450 from the power supply 440 can be a supply voltage that is provided on a chip by rectifier and/or regulator components the same chip. That is, the functional blocks in FIG. 4 shown as the power supply block 440 and controller block 450 need not be implemented as separated modules. Moreover, one or more of the functional modules described in FIG. 4 can be implemented by separately packaged chips electrically connected to one another.

Additionally or alternatively, the energy harvesting antenna 442 and the communication antenna 470 can be implemented with the same physical antenna. For example, a loop antenna can both harvest incident radiation for power generation and communicate information via backscatter radiation.

The external reader 480 includes an antenna 488 (or group of more than one antennae) to send and receive wireless signals 471 to and from the eye-mountable device 410. The external reader 480 also includes a computing system with a processor 486 in communication with a memory 482. The memory 482 is a non-transitory computer-readable medium that can include, without limitation, magnetic disks, optical disks, organic memory, and/or any other volatile (e.g. RAM) or non-volatile (e.g. ROM) storage system readable by the processor 486. The memory 482 can include a data storage 483 to store indications of data structures, such as sensor readings (e.g., from the analyte bio-sensor 462), program settings (e.g., to adjust behavior of the eye-mountable device and/or external reader 480), etc. The memory can also include program instructions 484 for execution by the processor 486 to cause the external reader to perform processes specified by the instructions 484. For example, the program instructions 484 can cause external reader 480 to provide a user-interface that allows for retrieving information communicated from the eye-mountable device 410 (e.g., sensor outputs from the analyte bio-sensor 462). The external reader 480 can also include one or more hardware components for operating the antenna 488 to send and receive the wireless signals 471 to and from the eye-mountable device 410. For example, oscillators, frequency injectors, encoders, decoders, amplifiers, filters, etc. can drive the antenna 488 according to instructions from the processor 486.

The external reader 480 can be a smart phone, digital assistant, or other portable computing device with wireless connectivity sufficient to provide the wireless communication link 471. The external reader 480 can also be implemented as an antenna module that can be plugged in to a portable computing device, such as in an example where the communication link 471 operates at carrier frequencies not commonly employed in portable computing devices. In some instances, the external reader 480 is a special-purpose device configured to be worn relatively near a wearer's eye to allow the wireless communication link 471 to operate with a low power budget. For example, the external reader 480 can be integrated in a piece of jewelry such as a necklace, earring, etc. or integrated in an article of clothing worn near the head, such as a hat, headband, etc.

In an example where the eye-mountable device 410 includes an analyte bio-sensor 462, the system 400 can be operated to monitor the analyte concentration in tear film on the surface of the eye. Thus, the eye-mountable device 410 can be configured as a platform for an ophthalmic analyte bio-sensor. The tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 400 configured as a tear film analyte monitor, the external reader 480 can emit radio frequency radiation 471 that is harvested to power the eye-mountable device 410 via the power supply 440. Radio frequency electrical signals captured by the energy harvesting antenna 442 (and/or the communication antenna 470) are rectified and/or regulated in the rectifier/regulator 446 and a regulated DC supply voltage 447 is provided to the controller 450. The radio frequency radiation 471 thus turns on the electronic components within the eye-mountable device 410. Once turned on, the controller 450 operates the analyte bio-sensor 462 to measure an analyte concentration level. For example, the sensor interface module 452 can apply a voltage between a working electrode and a reference electrode in the analyte bio-sensor 462 sufficient to cause the analyte to undergo an electrochemical reaction at the working electrode. The current through the working electrode can be measured to provide the sensor output indicative of the analyte concentration. The controller 450 can operate the antenna 470 to communicate the sensor results back to the external reader 480 (e.g., via the communication circuit 456). The sensor result can be communicated by, for example, modulating an impedance of the communication antenna 470 such that the modulation in impedance is detected by the external reader 480. The modulation in antenna impedance can be detected by, for example, backscatter radiation from the antenna 470.

In some embodiments, the system 400 can operate non-continuously ("intermittently") to supply energy to the eye-mountable device 410 to power the on-board controller 450 and electronics 460. For example, radio frequency radiation 471 can be supplied to power the eye-mountable device 410 long enough to carry out a tear film analyte concentration measurement and communicate the results. For example, the supplied radio frequency radiation can provide sufficient power to charge two electrodes to a potential sufficient to induce electrochemical reactions, measure the resulting amperometric current, and modulate the antenna impedance to adjust the backscatter radiation in a manner indicative of the measured current. In such an example, the supplied radio frequency radiation 471 can be considered an interrogation signal from the external reader 480 to the eye-mountable device 410 to request a measurement. By periodically interrogating the eye-mountable device 410 (e.g., by supplying radio frequency radiation 471 to temporarily turn the device on) and storing the sensor results (e.g., via the data storage 483), the external reader 480 can accumulate a set of analyte concentration measurements over time without continuously powering the eye-mountable device 410.

Figure 5A:
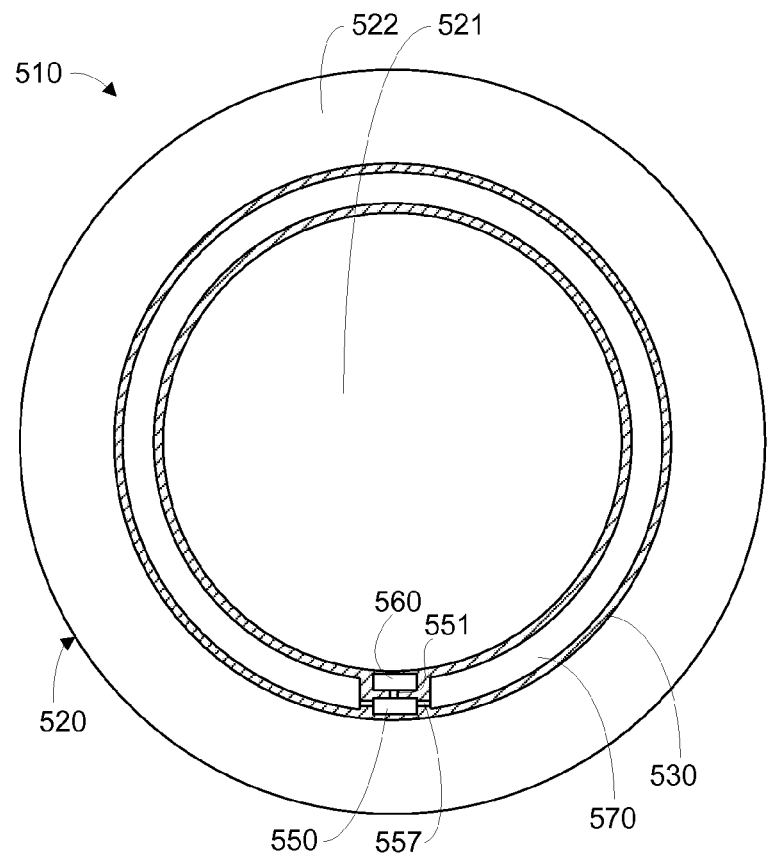
FIG. 5A is a top view of an example eye-mountable device, in accordance with an example embodiment.
Figure 5B:
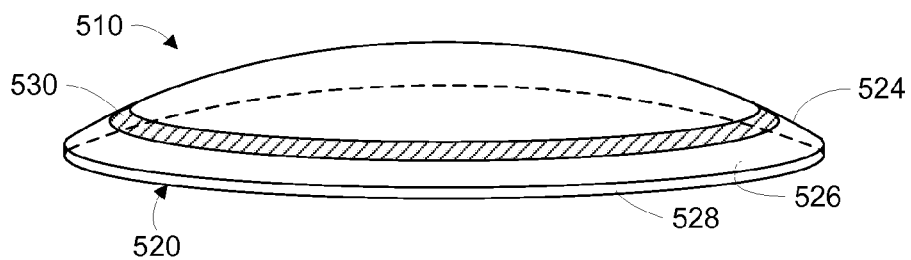
FIG. 5B is an aspect view of the example eye-mountable device shown in FIG. 5A.

FIG. 5A is a top view of an example eye-mountable electronic device 510. FIG. 5B is an aspect view of the example eye-mountable electronic device 510 shown in FIG. 5A. It is noted that relative dimensions in FIGS. 5A and 5B are not necessarily to scale, but have been rendered for purposes of explanation only in describing the arrangement of the example eye-mountable electronic device 510. The eye-mountable device 510 is formed of a polymeric material 520 shaped as a curved disk. The polymeric material 520 can be a substantially transparent material to allow incident light to be transmitted to the eye while the eye-mountable device 510 is mounted to the eye. The polymeric material 520 can be a biocompatible material similar to those employed to form vision correction and/or cosmetic contact lenses in optometry, such as polyethylene terephthalate ("PET"), polymethyl methacrylate ("PMMA"), silicone hydrogels, combinations of these, etc. The polymeric material 520 can be formed with one side having a concave surface 526 suitable to fit over a corneal surface of an eye. The opposing side of the disk can have a convex surface 524 that does not interfere with eyelid motion while the eye-mountable device 510 is mounted to the eye. A circular outer side edge 528 connects the concave surface 524 and convex surface 526.

The eye-mountable device 510 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 510 can be selected according to the size and/or shape of the corneal surface of the wearer's eye.

While the eye-mountable device 510 is mounted in an eye, the convex surface 524 (i.e., the anterior surface) faces outward to the ambient environment while the concave surface 526 (i.e., the posterior surface) faces inward, toward the corneal surface. The convex surface 524 can therefore be considered an outer, top surface of the eye-mountable device 510 whereas the concave surface 526 can be considered an inner, bottom surface. The "top" view shown in FIG. 5A is facing the convex surface 524.

A substrate (ring-shaped structure) 530 is embedded in the polymeric material 520. The substrate 530 can be embedded to be situated along the outer periphery 522 of the polymeric material 520, away from the center region 521. The substrate 530 does not interfere with vision because it is too close to the eye to be in focus and is positioned away from the center region 521 where incident light is transmitted to the eye-sensing portions of the eye. Moreover, the substrate 530 can be formed of a transparent material to further mitigate any effects on visual perception.

The substrate 530 can be shaped as a flat, circular ring (e.g., a disk with a central hole). The flat surface of the substrate 530 (e.g., along the radial width) is a platform for mounting electronics such as chips (e.g., via flip-chip mounting) and for patterning conductive materials (e.g., via deposition techniques) to form electrodes, antenna(e), and/or connections. The substrate 530 and the polymeric material 520 can be approximately cylindrically symmetric about a common central axis. The substrate 530 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only. The substrate 530 can be implemented in a variety of different form factors. In some examples, the substrate 530 may take the form of a full ring. In other examples, the substrate 530 may take the form of a partial ring, a segment of a ring, an annulus, or other geometries.

A loop antenna 570, controller 550, and bio-interactive electronics 560 are disposed on the embedded substrate 530. The controller 550 can be a chip including logic elements configured to operate the bio-interactive electronics 560 and the loop antenna 570. The controller 550 is electrically connected to the loop antenna 570 by interconnects 557 also situated on the substrate 530. Similarly, the controller 550 is electrically connected to the bio-interactive electronics 560 by an interconnect 551. The interconnects 551, 557, the loop antenna 570, and any conductive electrodes (e.g., for an electrochemical analyte bio-sensor, etc.) can be formed from conductive materials patterned on the substrate 530 by a process for precisely patterning such materials, such as deposition or lithography. The conductive materials patterned on the substrate 530 can be, for example, gold, platinum, palladium, titanium, carbon, aluminum, copper, silver, silver-chloride, conductors formed from noble materials, metals, combinations of these, etc.

With reference to FIG. 5A, which is a view facing the convex surface 524 of the eye-mountable device 510, the bio-interactive electronics module 560 is mounted to a side of the substrate 530 facing the convex surface 524. Where the bio-interactive electronics module 560 includes an analyte bio-sensor, for example, mounting such a bio-sensor on the substrate 530 to be close to the convex surface 524 allows the bio-sensor to sense analyte concentrations in tear film near the anterior surface of the device. However, the electronics, electrodes, etc. situated on the substrate 530 can be mounted to either the "inward" facing side (e.g., situated closest to the concave surface 526 when the thin polymer layer is located on the posterior side of the eye-mountable device) or the "outward" facing side (e.g., situated closest to the convex surface 524 when the thin polymer layer is located on the anterior side of the eye-mountable device). Moreover, in some embodiments, some electronic components can be mounted on one side of the substrate 530, while other electronic components are mounted to the opposing side, and connections between the two can be made through conductive materials passing through the substrate 530.

The loop antenna 570 is a layer of conductive material patterned along the flat surface of the substrate to form a flat conductive ring. In some instances, the loop antenna 570 can be formed without making a complete loop. For instance, the loop antenna can have a cutout to allow room for the controller 550 and bio-interactive electronics 560, as illustrated in FIG. 5A. However, the loop antenna 570 can also be arranged as a continuous strip of conductive material that wraps entirely around the flat surface of the substrate 530 one or more times. For example, a strip of conductive material with multiple windings can be patterned on the side of the substrate 530 opposite the controller 550 and bio-interactive electronics 560. Interconnects between the ends of such a wound antenna (e.g., the antenna leads) can be passed through the substrate 530 to the controller 550.

FIG. 5C is a side cross-section view of the example eye-mountable electronic device 510 while mounted to a corneal surface 22 of an eye 10. FIG. 5D is a close-in side cross-section view enhanced to show the tear film layers 40, 42 surrounding the exposed surfaces 524, 526 of the example eye-mountable device 510. It is noted that relative dimensions in FIGS. 5C and 5D are not necessarily to scale, but have been rendered for purposes of explanation only in describing the arrangement of the example eye-mountable electronic device 510. For example, the total thickness of the eye-mountable device can be about 200 micrometers, while the thickness of the tear film layers 40, 42 can each be about 10 micrometers, although this ratio may not be reflected in the Figures.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The motion of the eyelids 30, 32 distributes a tear film across the exposed corneal surface 22 of the eye 10. The tear film is an aqueous solution secreted by the lacrimal gland to protect and lubricate the eye 10. When the eye-mountable device 510 is mounted in the eye 10, the tear film coats both the convex and concave surfaces 524, 526 with an inner layer 40 (along the concave surface 526) and an outer layer 42 (along the convex layer 524). The tear film layers 40, 42 can be about 10 micrometers in thickness and together account for about 10 microliters.

The tear film layers 40, 42 are distributed across the corneal surface 22 and/or the convex surface 524 by motion of the eyelids 30, 32. For example, the eyelids 30, 32 raise and lower, respectively, to spread a small volume of tear film across the corneal surface 22 and/or the convex surface 524 of the eye-mountable device 510. The tear film layer 40 on the corneal surface 22 also facilitates mounting the eye-mountable device 510 by capillary forces between the concave surface 526 and the corneal surface 22. In some embodiments, the eye-mountable device 510 can also be held over the eye in part by vacuum forces against corneal surface 22 due to the concave curvature of the eye-facing concave surface 526.

As shown in the cross-sectional views in FIGS. 5C and 5D, the substrate 530 can be inclined such that the flat mounting surfaces of the substrate 530 are approximately parallel to the adjacent portion of the convex surface 524. As described above, the substrate 530 is a flattened ring with an inward-facing surface 532 (facing the concave surface 526 of the polymeric material 520) and an outward-facing surface 534 (facing the convex surface 524). The substrate 530 can have electronic components and/or patterned conductive materials mounted to either or both mounting surfaces 532, 534.

As shown in FIG. 5D, the bio-interactive electronics 560, controller 550, and conductive interconnect 551 are mounted on the outward-facing surface 534 such that the bio-interactive electronics 560 are facing the convex surface 524. As described above, the polymer layer defining the anterior side may be less than 50 micrometers thick, whereas the polymer layer defining the posterior side may be thicker. Thus, the bio-interactive electronics 560 may be less than 50 micrometers away from the convex surface 524 and may be a greater distance away from the concave surface 526. However, in other examples, the bio-interactive electronics 560 may be mounted on the inward-facing surface 532 of the substrate 530 such that the bio-interactive electronics 560 are facing the concave surface 526. The bio-interactive electronics 560 could also be positioned closer to the concave surface 526 than the convex surface 524.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

What is claimed is:

1. A method comprising:
    applying a first amount of polymerizable material to a ring-shaped structure, wherein the ring-shaped structure comprises at least one sensor;
    positioning the ring-shaped structure with the first amount of polymerizable material applied thereto in a mold, wherein the mold is configured to form an eye-mountable device;
    applying pressure, via a plunger comprising a compliant material, on the ring-shaped structure in the mold while curing the first amount of polymerizable material;
    adding a second amount of polymerizable material to the mold with the ring-shaped structure therein; and
    curing the second amount of polymerizable material to form an over-molded polymer layer such that the ring-shaped structure is at least partially enclosed in the eye-mountable device.

2. The method of claim 1, wherein positioning the ring-shaped shaped structure with the first amount of polymerizable material applied thereto in the mold comprises positioning the ring-shaped structure with the first amount of polymerizable material applied thereto on a previously-formed polymer layer in the mold.

3. The method of claim 2, wherein the previously-formed polymer layer defines an anterior side of the eye-mountable device and the over-molded polymer layer defines a posterior side of the eye-mountable device.

4. The method of claim 2, wherein the previously-formed polymer layer is in a partially-cured state.

5. The method of claim 2, wherein the previously-formed polymer layer and the over-molded polymer layer comprise a transparent material.

6. The method of claim 1, wherein applying the first amount of polymerizable material to the ring-shaped structure comprises placing the polymerizable material at one or more discrete locations on the ring-shaped structure, and wherein applying pressure on the ring-shaped structure comprises applying pressure at the one or more discrete locations.

7. The method of claim 1, wherein applying pressure on the ring-shaped structure comprises applying pressure on the entire ring-shaped structure.

8. The method of claim 1, wherein the over-molded polymer layer comprises a hydrogel material or a silicone elastomer.

9. A method comprising:
    applying a first amount of polymerizable material to a ring-shaped structure, wherein the ring-shaped structure comprises at least one sensor;
    positioning the ring-shaped structure with the first amount of polymerizable material applied thereto on a previously-formed polymer layer in a mold, wherein the mold is configured to form an eye-mountable device;
    applying, via a plunger comprising an elastic material, pressure on the ring-shaped structure in the mold; and
    adding a second amount of polymerizable material to the mold with the ring-shaped structure therein, and curing the second amount of polymerizable material to form an over-molded polymer layer such that the ring-shaped structure is fully enclosed in the eye-mountable device.

10. The method of claim 9, wherein the previously-formed polymer layer defines an anterior side of the eye-mountable device and the over-molded polymer layer defines a posterior side of the eye-mountable device.

11. The method of claim 9, wherein the anterior side of the eye-mountable device is configured to allow an analyte to diffuse therethrough to be detected by the sensor.

12. The method of claim 9, wherein the previously-formed polymer layer is in a partially-cured state.

13. The method of claim 9, wherein the previously-formed polymer layer and the over-molded polymer layer comprise a transparent material.

14. The method of claim 9, wherein the ring-shaped structure is more rigid than the previously-formed polymer layer and the over-molded polymer layer.

15. The method of claim 9, wherein applying the first amount of polymerizable material to the ring-shaped structure comprises placing the polymerizable material on one or more discrete locations on the ring-shaped structure, and wherein applying pressure on the ring-shaped structure comprises applying pressure at the one or more discrete locations.

16. The method of claim 9, wherein applying pressure on the ring-shaped structure comprises applying pressure on the entire ring-shaped structure.

17. The method of claim 9, wherein applying pressure on the ring-shaped structure comprises applying pressure while curing the first amount of polymerizable material.

18. A method comprising:
    applying an amount of adhesive material to a ring-shaped structure, wherein the ring-shaped structure comprises at least one sensor;
    positioning the ring-shaped structure with the amount of adhesive material applied thereto in a mold, wherein the mold is configured to form an eye-mountable device;
    applying pressure, via a plunger comprising a compliant material, on the ring-shaped structure in the mold while curing the amount of adhesive material;
    adding a respective amount of polymerizable material to the mold with the ring-shaped structure therein; and
    curing the respective amount of polymerizable material to form an over-molded polymer layer such that the ring-shaped structure is at least partially enclosed in the eye-mountable device.

19. The method of claim 18, wherein the adhesive material comprises a thermosetting polymer.

* * * * *